United States Patent [19]

Ryan et al.

[11] Patent Number: 5,432,089
[45] Date of Patent: Jul. 11, 1995

[54] REFERENCE CONTROL FOR USE WITH MANUAL AND FLOW CYTOMETRIC RETICULOCYTE COUNTING DEVICES

[75] Inventors: Wayne L. Ryan, Omaha, Nebr.; Alireza Ebrahim, Irvine, Calif.

[73] Assignee: Streck Laboratories, Inc., Omaha, Nebr.

[21] Appl. No.: 146,658

[22] Filed: Nov. 2, 1993

Related U.S. Application Data

[63] Continuation of Ser. No. 128,052, Sep. 27, 1993, abandoned, which is a continuation of Ser. No. 844,162, Mar. 2, 1992, abandoned.

[51] Int. Cl.⁶ ............................................ G01N 33/49
[52] U.S. Cl. ................................. 436/10; 436/8; 436/16; 436/63; 436/174; 435/2; 435/6; 435/29
[58] Field of Search ................ 436/8, 10, 11, 16–19, 436/63, 174, 176; 435/2, 6, 29; 252/380

[56] References Cited

U.S. PATENT DOCUMENTS

| | | | |
|---|---|---|---|
| 4,062,949 | 12/1977 | Tung et al. | 514/8 |
| 4,224,313 | 9/1980 | Zimmermann et al. | 435/2 X |
| 4,289,756 | 9/1981 | Zimmermann et al. | 436/10 X |
| 4,327,710 | 5/1982 | DeLoach et al. | 604/5 |
| 4,478,824 | 10/1984 | Franco et al. | 435/2 X |
| 4,517,080 | 5/1985 | DeLoach et al. | 210/85 |
| 4,652,449 | 3/1987 | Ropars et al. | 435/2 X |
| 4,752,586 | 6/1988 | Ropars et al. | 435/287 |
| 4,777,139 | 10/1988 | Wong et al. | 436/18 |
| 4,931,276 | 6/1990 | Franco et al. | 435/2 X |
| 4,994,375 | 2/1991 | Posner et al. | 436/18 X |
| 5,132,223 | 7/1992 | Levine et al. | 435/240.3 X |

OTHER PUBLICATIONS

Leung, P, et al., "Encapsulation of Thiosulfate: Cyanide Sulfurtransferase by Mouse Erythrocytes," *Toxicol. App. Pharm.* 83:101–107 (1986).
DeLoach, J. R., "In Vivo Survival of [C]sucrose-loaded Porcine Carrier Erythrocytes," *Am. J. Vet. Res.* 44:1159–1161 (1983).
DeLoach, J. R. et al., "Preparation of Resealed Carrier Erythrocytes and In Vivo Survival in Dogs," *Am. J. Vet. Res.* 42:667–669 (1981).
Fiddler, M. B. et al., "XIV. Comparison of Methods for Enzyme Entrapment in Human Erythrocytes," *J. Lab. Clin. Med.* 96:307–317 (1980).
Deloach, J. R. et al., "A Dialysis Procedure for Loading Erythrocytes with Enzymes and Lipids," *Biochem. Byophys. Acta* 496:136–145 (1977).
Keren, D. F., ed. "Flow Cytometry In Clinical Diagnosis," ASCP Press, Am. Society of Clinical Pathologists, Chicago.
Tonetti, M. et al., "Carrier Erthrocytes Clinical Pharmocakinetic Consideration," *Clin. Pharmacokinet.* 25(5):351–357 (1993).
DeLoach, J. R. et al., "An Erythrocyte Encapsulator Dialyzer Used in Preparing Large Quantities of Erythrocyte Ghosts and Encapsulation of a Pesticide in Erythrocyte Ghosts," *Anal. Biochem.* 102:220–227 (1980).
Yamaguchi, T. et al., "Effects of Drugs, Salts, and Phospholipid Vesicles on Hemoglobin Release from Hydrostatic Pressure–Treated Human Erythrocytes," *J. Biochem.* 113:513–518 (1993).
Ihler, G. M. "Potential Use of Erythrocytes as Carriers for Enzymes and Drugs," pp. 130–153, *Drug Carriers*, Ed. Gregory Gregoriadis; Academic Press, (N.Y., 1979).
DeLoach, J. R. et al., "Circulating Carrier Erythrocytes: Slow–Release Vehicle for an Antileukemic Drug, Cytosine Arabinoside," *Am. J. Vet. Res.* 43:2210–2212 (1982).
Auer, D. et al., "Loading of Human Red Blood Cells with DNA and RNA," *Z. Naturforsch.* 31c:149–157 (1976).
Kinosita, Jr., K. et al., "Formation and Resealing of Pores of Controlled Sizes in Human Erythrocytes Membrane," *Nature* 268:438–441 (1977).

*Primary Examiner*—James C. Housel
*Assistant Examiner*—Maureen M. Wallenhorst
*Attorney, Agent, or Firm*—Harness, Dickey & Pierce

[57] ABSTRACT

A stable reticulocyte reference control which may be used with both manual and flow cytometric reticulocyte counting devices is provided. The reference control contains erythrocytes loaded with nucleic acids or polyanions capable of binding with a cationic dye. The loaded erythrocytes are suspended in an aqueous preserving medium. Methods of making and using the reticulocyte reference control are also provided.

17 Claims, 5 Drawing Sheets

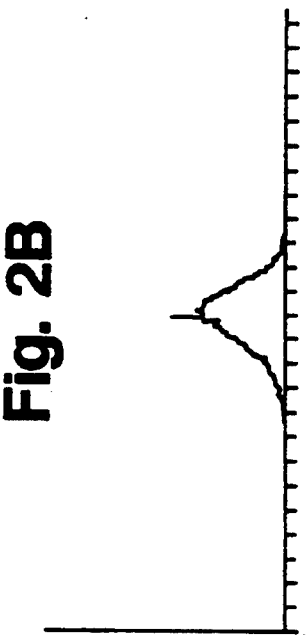
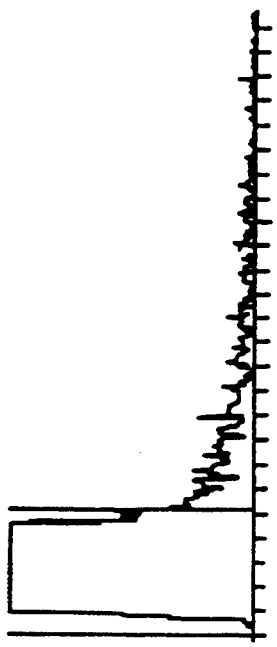
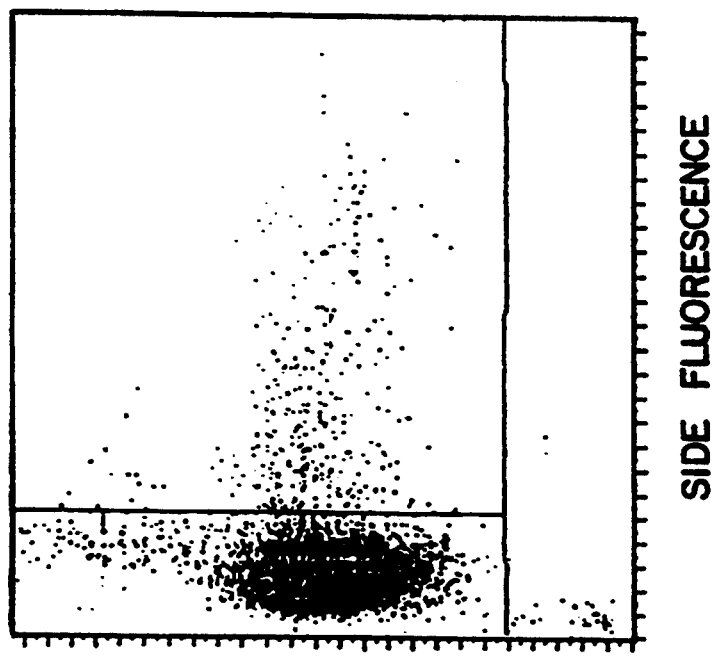

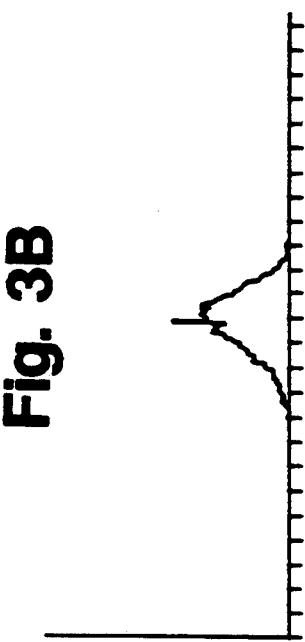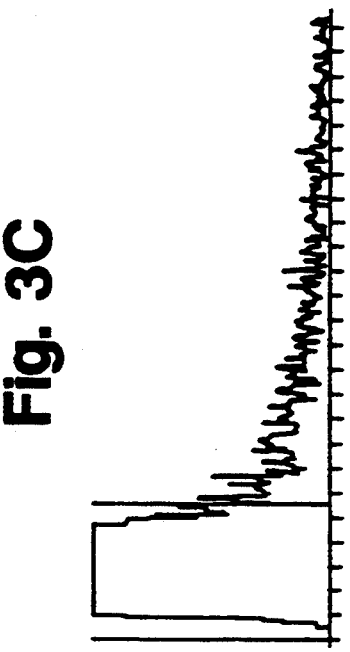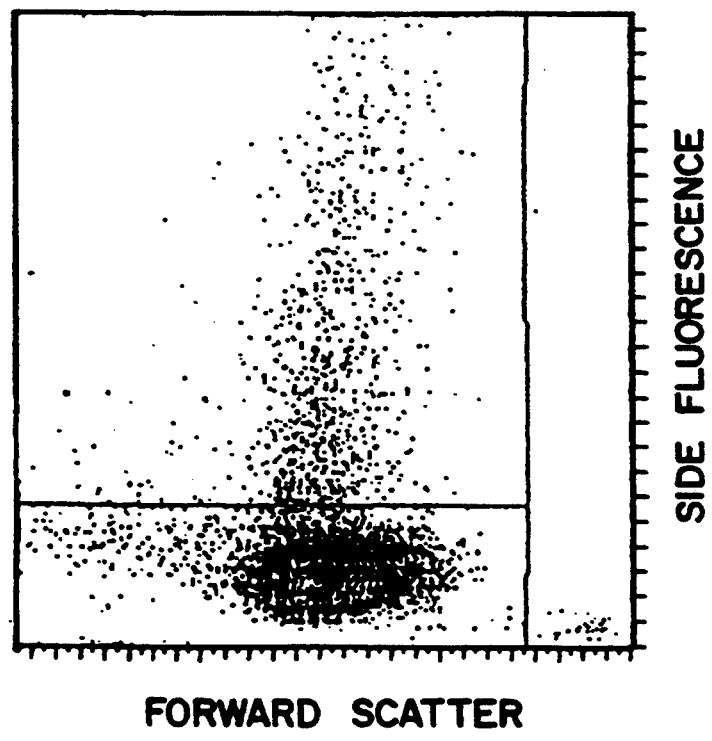

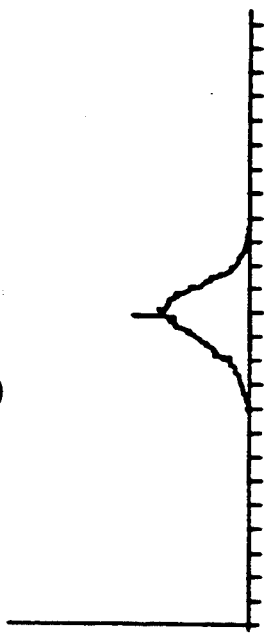
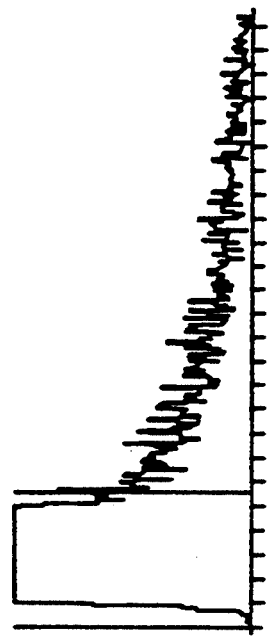
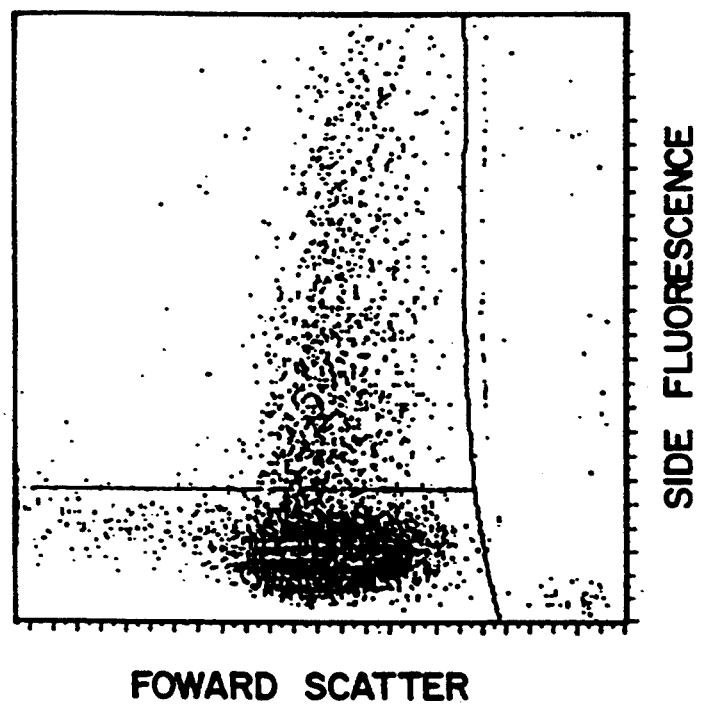

REFERENCE CONTROL FOR USE WITH MANUAL AND FLOW CYTOMETRIC RETICULOCYTE COUNTING DEVICES

CONTINUING APPLICATION INFORMATION

This application claims priority from PCT/US93/01839, filed Mar. 1, 1993. This application is also a continuation of U.S. Ser. No. 08/128,052, filed Sep. 27, 1993, now abandoned which is a continuation of U.S. Ser. No. 07/844,162, filed Mar. 2, 1992, now abandoned.

FIELD OF THE INVENTION

This invention relates in general to a multilevel reticulocyte reference control for use with either manual or flow cytometric reticulocyte counting devices and in particular to a reticulocyte reference control containing erythrocytes loaded with a nucleic acid or a polyanion and a method for its use in assessing manual and instrumental reticulocyte analyses that are currently being used in clinical laboratories.

BACKGROUND OF THE INVENTION

Reticulocytes are immature red blood cells (or RBCs) containing residual cytoplasmic ribosomes which are formed when developing red blood cells extrude their nuclei into the bone marrow under normal hemopoietic conditions. These cells spend two to three days in bone marrow prior to being released into the peripheral blood circulation and one to two days in circulation before losing their ribonucleic acid (RNA) content and reaching maturity. The reticulocyte population in the peripheral blood is approximately 1% of the total erythrocyte population in normal subjects, and the majority of the reticulocytes are of mature form. The hormone erythropoietin, which stimulates and regulates erythrocyte production, is responsible for the release of the reticulocytes from the bone marrow. Young reticulocytes contain larger quantities of RNA, and this characteristic can be employed to distinguish mature and immature reticulocytes.

Reticulocyte counting is a valuable blood test, and it is very widely done. The number of reticulocytes in peripheral blood circulation is used to study and evaluate erythropoietic activity of bone marrow. Subjects with suppressed bone marrow activity, e.g., those patients undergoing chemotherapy, exhibit a lower reticulocyte percentage and a higher mature reticulocyte population. Conversely, those patients with stimulated bone marrow function, such as individuals with hemolytic anemia, show higher reticulocyte percentage and a lower mature reticulocyte population than those observed in normal and healthy subjects.

Reticulocyte identification and enumeration is based on the finding of residual ribosomes and nucleic acid in early nonnucleated red blood cells. This diagnostic test has long been done manually by staining and precipitating residual ribonucleic acid with dyes such as new methylene blue and brilliant cresyl blue. The precipitated RNA will appear either as cytoplasmic dots or filaments under microscope. Unfortunately, the manual reticulocyte test has long been known for its poor accuracy and precision. Irregular staining and random distribution of reticulocytes on the blood film, variations in the preparation of the stained film and the stain used, presence of artifacts resulting from precipitation of free and unbound dye, poor microscope focus, and differences in definition of the reticulocytes are some of the factors that can introduce error or contribute to the inaccuracy of manual reticulocyte counting. However, another problem with manual techniques is that suitable, long-lasting, highly accurate reference controls are often lacking.

In recent years, automated reticulocyte counting has been possible due to advances in flow cytometry. Flow cytometric analysis of reticulocytes depends on the binding of suitable fluorescent dyes to residual ribosomes and nucleic acid. Excitation of the stained cells with a laser beam and detection of forward scatter and side fluorescence provides information on size and nucleic acid content of red blood cells. Acridine orange, auramine O, pyronine Y, thioflavin T, and propidium iodide have been used in flow cytometric reticulocyte counting methods. These dyes provide sufficient resolution between reticulocytes and background erythrocytes for on-line instrumental reticulocyte analyses.

Because of these newer flow cytometric techniques, higher degrees of precision have been obtained for instrumental reticulocyte analysis. One reason for the better precision of the automated analysis is that many more cells can be counted per analysis than only the roughly 1000 cells that are counted in the manual analysis. Also, the instrumental method of flow cytometry involves setting the threshold to exclude mature red blood cells which is an objective method as compared to the manual method in which the identification of reticulocytes is a subjective decision.

However, the flow cytometry procedures currently used also rely on reference controls that suffer from various inaccuracies and which cannot be used with manual analyses. In particular, the reticulocyte reference controls used in these procedures commonly involve the binding of various fluorochromes to RBCs or polymer particles which produces certain inaccurracies and which results in a Gaussian reticulocyte distribution on the flow cytometers.

At present, there is thus an absence of a highly accurate reticulocyte reference control which can be used in assessment of bone marrow activity and in maximizing quality control with regard to cytometric procedures involving blood cells. Further, there is a lack of adequate reference control materials which are highly reliable, long-lasting and which can be used in both manual and flow cytometric techniques used to monitor a variety of diseases and therapeutic treatments involving blood cells. It is thus highly desirable to obtain a suitable reference control by which reticulocyte count can be accurately determined, and it is also desirable that such a reference control be suitable for use with both manual and flow cytometers.

It is presently known to employ a reversible osmotic lysis procedure in order to encapsulate various compounds into erythrocytes. In such a procedure, red blood cells are hypotonically dialyzed in the presence of the desired compound, such as enzyme, so that the erythrocytes swell up and form pores of sufficient size so that the desired compound enters the cells. The treatment with hypotonic solution is followed by hypertonic dialysis to reseal the pores formed on the cell membrane so as to encapsulate or entrap the desired compound inside the cells. This process is disclosed in a variety of patents and other references, including, e.g., U.S. Pat. Nos. 4,931,276 and 4,652,449, *Am. J. Vet. Res.* 44:1159 (1983), *Am. J. Vet. Res.* 42:667 (1981), *Toxicol. App.*

Pharm. 83:101 (1986) and *Biochim. Biophys. Acta* 496:136 (1977), all incorporated herein by reference.

Although these loaded erythrocytes have been used in specific biotherapeutic applications such as enzyme therapy and other methods wherein specific compounds are introduced into the blood stream (see, e.g., *J. Lab. Clin. Med.* 96:307 (1980), incorporated herein by reference), the use of such loaded erythrocytes as reference controls for cytometric procedures has not previously been disclosed or suggested. It has recently been discovered by the inventors that such loaded erythrocytes can be successfully used to prepare a reliable, stable and accurate reference control that can be used in both manual and flow cytometric techniques such as the counting of reticulocytes.

SUMMARY OF THE INVENTION

It is thus an object of the present invention to provide a reference control which is suitable for use with both manual and flow cytometers and which can provide an accurate control for cytometric tests of bone marrow activity.

It is further an object of the present invention to provide a multi-level reference control which can be utilized with a wide variety of reticulocyte identification and enumeration methods presently employed in clinical laboratories.

It is still further an object of the present invention to employ encapsulated nucleic acids and suitable polyanions into a reference control that can be used with both flow cytometric and manual reticulocyte counting procedures.

These and other objects of the present invention are achieved through the provision of a reticulocyte reference control which is usable with both manual and flow cytometric reticulocyte counting devices and which comprises erythrocytes loaded with a nucleic acid or a polyanion capable of binding with a cationic dye in an aqueous preserving medium. In the preferred method of the invention, an osmotic lysis procedure is used to prepare the reference control by encapsulating the nucleic acid or the polyanion inside the erythrocyte, and the resulting reference control can be used with a wide variety of cytometric counting devices to provide an accurate picture of bone marrow activity.

BRIEF DESCRIPTION OF THE DRAWING FIGURES

FIGS. 2A–2C are graphic representations of Sysmex R-1000 cytograms and histograms obtained using a reticulocyte reference control of the present invention at three different reticulocyte levels. 2A shows 1.59% reticulocytes.

FIGS. 3A–3C are graphic representations of Sysmex R-1000 cytograms and histograms obtained using a reticulocyte reference control of the present invention at three different reticulocyte levels. 3A shows 3.13% reticulocytes.

FIGS. 4A–4C are graphic representations of Sysmex R-1000 cytograms and histograms obtained using a reticulocyte reference control of the present invention at three different reticulocyte levels. 4A shows 5.08% reticulocytes.

DETAILED DESCRIPTION OF THE PREFERRED EMBODIMENTS

Figure 1:
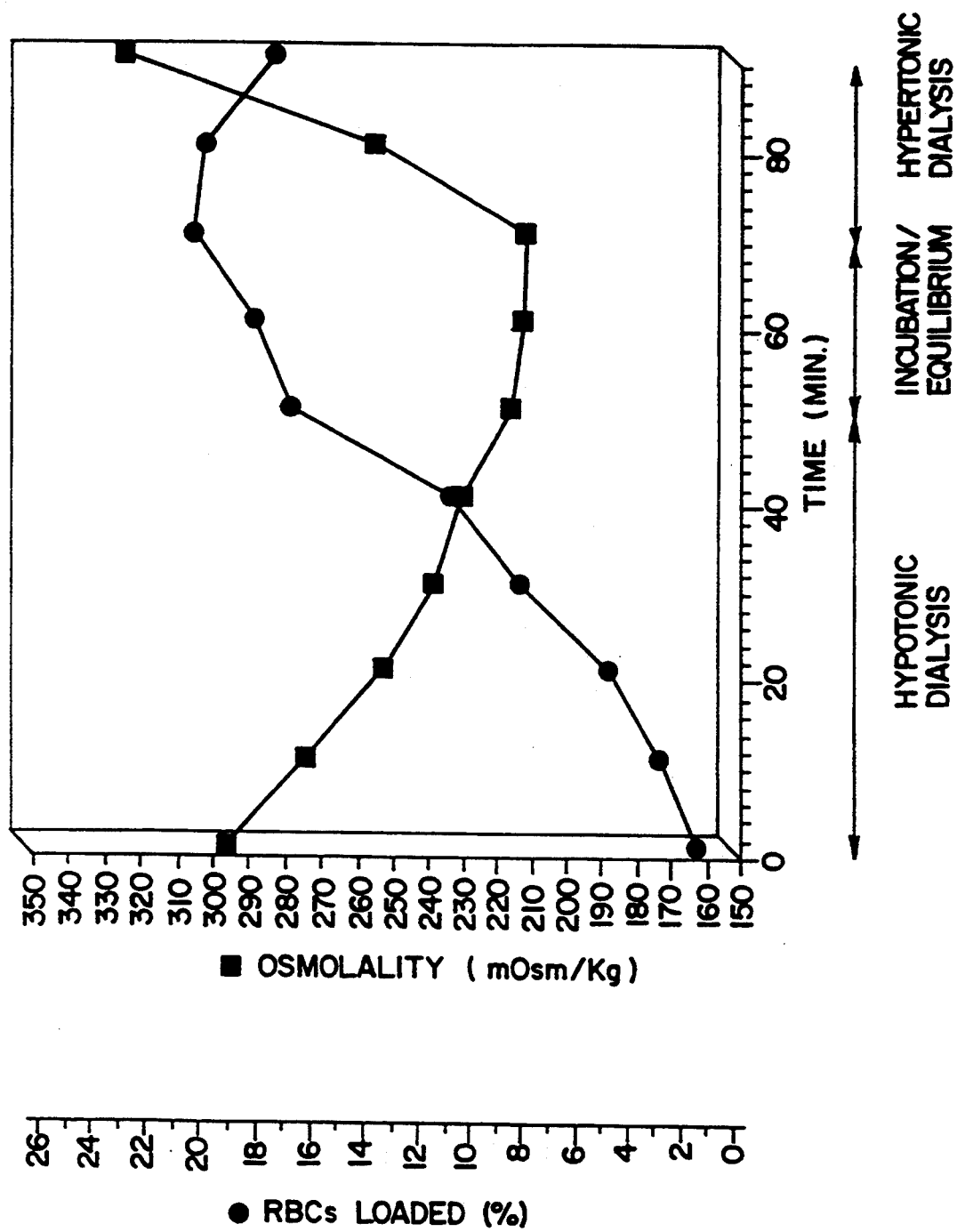
FIG. 1 is a graphic representation of changes in osmolality and the percentage of erythrocytes loaded during an RNA encapsulation procedure in accordance with the present invention.

In accordance with the present invention, there is provided a reticulocyte reference control that comprises loaded erythrocytes in an aqueous preserving medium, and in the preferred embodiments, the encapsulation or loading is carried out using reversible osmotic lysis techniques. In one preferred embodiment of the invention, the erythrocytes that will be used as a reference control will be loaded with a nucleic acid such as ribonucleic acid (RNA) or deoxyribonucleic acid (DNA). In a particularly preferred embodiment, the encapsulated RNA is prepared from yeast such as Torula Yeast. The morphology of the nucleic acid-loaded erythrocytes used in the reference control will be similar to that of normal erythrocytes and reticulocytes, with the loaded RBCs being generally slightly smaller than RBCs used for diluting. In addition, the RBCs loaded in this manner have a broader size distribution.

The morphology of cells loaded in the invention are somewhat smaller and have a greater size distribution than non-loaded cells.

In a second preferred embodiment, it is possible to provide a suitable reference control containing erythrocytes that have been loaded with polyanions, particularly those polyanions that are capable of binding to a cationic dye. One particularly preferred polyanion suitable for use in the invention is heparin. It is preferred that the polyanions to be used in the present invention will have molecular weights comparable to that of RNA, and will generally range from about 10,000 to 100,000 daltons. Other polyanions contemplated for use in the present invention include those disclosed in U.S. Pat. No. 4,931,276, incorporated herein by reference. Polyanion-loaded erythrocytes are morphologically similar to RNA-encapsulated RBCs and have similar reticulocyte characteristics as well. The polyanion-containing RBCs are suitable in the invention because of the many cationic stains that are used for both manual and flow cytometric reticulocyte analysis.

In the preferred embodiment, the loaded RBCs of the invention will be washed and preserved in a suitable aqueous preserving medium in order to form the reference control of the invention. It is preferred that the aqueous medium be formulated without phosphate ion and prepared so as to yield a cytogram/scattergram similar to that of fresh whole blood. In the preferred embodiment, the aqueous preserving medium is comprised of disodium salt of EDTA, magnesium gluconate, polyethylene glycol (preferably with an average mol. wt. of about 20,000), methyl paraben, neomycin sulfate and nalidixic acid. The loaded RBCs can also be diluted with appropriate volumes of fresh and previously non-loaded equilibrated RBCs in this aqueous medium in order to prepare suitable erythrocyte samples at various reticulocyte levels as will be discussed further below. Preferably, the pH for this medium is about 6.5–7.0 (6.68–6.72 particularly preferred), and the osmolality should be about 300–350 mOsm/Kg (320–330 particularly preferred).

In the preferred embodiment, the loaded RBCs of the invention are prepared using any of the many known reversible osmotic lysis procedures such as the ones disclosed in the references incorporated above. In the general mode of these operations, red blood cells are hypotonically dialyzed in the presence of the desired compound, in this case either a nucleic acid or a suitable polyanion, so that the erythrocytes swell up and form pores of sufficient size so that the desired compound enters the cells. The treatment with hypotonic solution is followed by hypertonic dialysis to reseal the pores formed on the cell membrane so as to encapsulate or entrap the desired compound inside the cells.

In one preferred mode in accordance with the present invention, the osmotic lysis process is carried out by first washing packed RBCs in an isotonic solution. Next, the RNA is added to the RBC solution along with a hemolysate (preferably prepared from packed and sonicated erythrocytes), the solution is mixed to form a suspension, and then a dialysis chamber is prepared with a hypotonic solution of preferably under about 30 mOsm/Kg osmolality. The RBC suspension can then be placed in a dialysis bag which is put into the hypotonic solution. The dialysis bag is mixed and the osmolality is checked regularly to ensure that entrapment is taking place efficiently. When the osmolality of the dialysis bag is about 180 mOsm/Kg, the hypotonic solution is discarded and the RBC suspension is allowed to equilibrate at room temperature. Next, a hypertonic solution (having osmolality preferably greater than about 850 mOsm/Kg) is placed in the dialysis chamber, and the RBCs in the dialysis bag undergo resealing of their cell membranes. The resealing step can be stopped when isotonicity (at roughly about 300 mOsm/Kg) is restored.

After loaded RBCs are obtained in this manner, they then can be formed into reference controls in accordance with the present invention which are suitable for use with both manual and flow cytometric devices and techniques associated with reticulocyte counting. In the preferred mode, the suspension obtained above is centrifuged so that the RBCs can be recovered, and the recovered RNA-loaded RBCs are added to a suitable aqueous preserving medium, such as the one prepared as described above. The medium is selected so that the loaded RBCs will yield cytogram/scattergram patterns similar to that of fresh whole human blood when equilibrated in the medium. The loaded RBCs can be diluted with appropriate volumes of the medium so that reference samples can be obtained which correspond to various reticulocyte levels. Once the reference control of the invention is obtained, it can be used in any of the many conventional reticulocyte staining and counting procedures currently in use, such as those referred to above. For example, the reference control of the present invention and sample of interest may be stained and compared, to detect reticulocytes in the sample. In addition, the reference control of the invention will be suitable for a variety of other similar cytometric procedures, as would be obvious to one skilled in the art.

The present invention thus provides a suitable multi-level reticulocyte reference control which can be used accurately to assess both manual and instrumental reticulocyte analyses and which can operate with the many types of both manual and flow cytometers that are presently in use.

The following specific example is presented as illustrative of the present invention and is not intended to limit its scope in any way:

EXAMPLE

In the particularly preferred mode of operation of the present invention, the first step in preparing the reference control of the invention is the separation and filtration of erythrocytes that are to be used for the encapsulation. In this example, this is accomplished using blood obtained from human sources, but other suitable erythrocytes obtained from other animals will also be suitable for particular applications. In the preferred process, the RBCs from the blood obtained from human sources are separated by conventional methods known in the art.

Once separated, the RBCs are stored in a diluent specially formulated to destroy weak and old RBCs for a suitable time period, such as about one day. Weak and old cells are not suitable for reversible osmotic lysis because they cannot tolerate the sudden change in osmotic concentration that occurs during the hypotonic expansion of the RBCs. The surviving RBCs are later filtered through a 20 $\mu$m high capacity transfusion filter to remove microaggregates and debris from the RBCs prior to encapsulation. Separation and filtration of erythrocytes as well as other procedure used in this invention are preferably carried out under aseptic conditions and at room temperature.

Next, the obtained erythrocytes are washed after filtration. In this step, filtered RBCs are concentrated by centrifugation for 15 minutes at 350Xg and then divided into two portions. One portion is washed with equal volumes of an isotonic solution containing 144 mM NaCl, 2 mM MgCl$_2$, and 5 mM D-(+)-glucose (pH=7.3 and osmolality=290 mOsm/Kg) three times, and after washing, the RBCs are packed to $>7\times10^6$ cells/$\mu$L by centrifugation and later used for encapsulation and preparation of hemolysate. The second portion is washed with equal volumes of a preservative diluent containing 704 mg EDTA (disodium salt), 329 mg magnesium gluconate, 500 mg polyethylene glycol (avg. MW of 20,000), 40 mg methyl paraben, 40 mg neomycin sulfate, and 10 mg nalidixic acid (pH=6.70$\pm$0.02 and osmolality =325$\pm$5 mOsm/Kg) three times, and after washing, the RBCs are diluted with the same diluent to obtain a RBC count of 4.0$\times$10$^6$ RBCs//$\mu$L. These cells which will have a cytogram/scattergram similar to that of fresh whole human blood after 4 days of equilibration in this diluent will be used to dilute the loaded RBCs in the final step of present invention.

In this example, the nucleic acid RNA is encapsulated into the erythrocytes of the control. If desired, however, a polyanion could be encapsulated in a similar procedure. To encapsulate the RNA, an RNA solution (preferably 3.5 % wt.vol) is first prepared by dissolving an appropriate amount of RNA (from Torula Yeast) in distilled water. After the RNA is dissolved, the pH and the osmolality of the solution are adjusted to 7.3$\pm$0.1 and 290$\pm$10 mOsm/Kg, respectively.

It is also necessary to prepare a hemolysate. In preparing the hemolysate, erythrocytes are washed with isotonic solution, packed to $>7\times10^6$ RBCs/$\mu$L and sonicated for 5 minutes twice to rupture the cell membranes. The pH and the osmolality of the resulting hemolysate will be 7.3$\pm$0.1 and 290$\pm$10 mOsm/Kg, respectively. The hemolysate should contain 20$\pm$1 g hemoglobin/dL and is used without further removal of membrane. Red blood cell lysate with hemoglobin concentration of 20 g/dL is necessary for RNA entrapment to obtain RNA-encapsulated erythrocytes which resemble normal reticulocytes with similar reticulocyte continuum and distribution.

The prepared erythrocytes are now ready for encapsulation. In the preferred encapsulation process, packed RBCs ($>7 \times 10^6$ Cells/$\mu$L) washed with isotonic solution (2 volumes), RNA solution (1 volume), and hemolysate (1 volume) are gently mixed and allowed to stand at room temperature for 10 minutes with occasional mixing. During this time the dialysis container is filtered with 20 volumes of a hypotonic solution containing 4 mM MgCl2 and 5 mM glucose (pH=7.3 and osmolality <30 mOsm/Kg). A previously hydrated dialysis tubing (Spectra/Por 2, MWCO 12000-14000) is closed at one end by a dialysis tubing closure and mounted to a plastic funnel at the other end. This provides easy access to the tubing content. The dialysis tube is then secured in the dialysis container, and the hypotonic solution is stirred on a magnetic stirrer.

The RBCs/RNA/hemolysate suspension is then transferred to the dialysis bag for hypotonic lysis and entrapment of RNA. The content of the dialysis bag is mixed manually by introducing air bubbles using a disposable pipet every 10 minutes. Also, every 10 minutes, 500 $\mu$L RBCs are withdrawn from the dialysis bag and reused to measure osmolality and obtain cytograms. Cytograms and osmolality determinations are necessary to evaluate the efficiency of the RNA entrapment procedure.

The hypotonic solution is discarded when the inside osmolality of the dialysis bag reaches $180+10$ mOsm/Kg. The dialysis bag containing the RBCs/RNA/hemolysate is allowed to equilibrate at room temperature for 20 minutes. Following this incubation period, the dialysis container is filled with 20 volumes of a hypertonic solution containing 450 mM NaCl, 10mM Na$_2$, HPO$_4$, and 10 mM NaH$_2$PO$_4$ (pH=7.3 and osmolality >850 mOsm/Kg) to reseal the cell membrane. The resealing step is stopped when isotonicity is restored (at about 300 mOsm/Kg) by removing the dialysis bag from the dialysis tank containing the hypertonic solution.

The percentage of RBCs loaded and the change in osmolality during the hypotonic and hypertonic dialysis steps in a typical entrapment process can be monitored, and this is shown graphically in FIG. 1. As the osmotic concentration of the medium surrounding the RBCs decreases during the hypotonic dialysis step, the number of RBCs being loaded increases. The changes in the number of loaded RBCs have been monitored, and graphic analysis of these changes indicates that during the hypotonic dialysis, there is a population shift from the erythrocyte region of the cytogram to the reticulocyte region indicating increased RNA encapsulation in erythrocytes.

After the hypertonic resealing step is completed, the reticulocyte reference control of the invention can be prepared. In this process, the content of the dialysis bag is added to an equal volume of an isotonic and neutral solution, and the suspension is allowed to stand at room temperature for approximately 24 hours. The suspension is later centrifuged for 10 minutes at 350Xg, and the supernatant containing excess hemolysate and RNA is discarded. The RNA-loaded RBCs are washed with a diluent specially formulated to yield cytogram/scattergram similar to that of fresh whole human blood after 4 days of equilibration in this diluent. This diluent is composed of 704 mg EDTA (disodium salt), 329 mg magnesium gluconate, 500 mg polyethylene glycol (avg. MW of 20,000), 40 mg methyl paraben, 40 mg neomycin sulfate, and 10 mg nalidixic acid with final osmolality and pH of 325$\pm$5 mOsm/Kg and 6.70$\pm$0.02, respectively. The loaded and non-loaded RBCs are then incubated at 37° C. for 24 hours to stabilize the reticulocytes. Alternatively, the loaded and non-loaded RBC are held at 22° C. for three weeks to stabilize the reticulocytes. After incubation the loaded and non-loaded RBCs are separately washed with the above preservative diluent again and allowed to equilibrate for one week at 6° C. These RNA-encapsulated RBCs are later diluted with appropriate volumes of non-loaded RBCs in the same diluent to prepare erythrocyte samples with various reticulocyte levels. Typical cytograms and histograms of dilute RNA-loaded RBCs at 3 reticulocyte levels which can be used as multi-level reticulocyte reference controls for manual and automated reticulocyte analysis are depicted in FIGS. 2-4.

The morphology of the RNA-loaded erythrocytes used for preparation of the reference control of the invention is similar to those of normal erythrocytes and reticulocytes. However, the RNA-encapsulated RBCs are usually slightly smaller than the RBCs used for diluting. Also, the RNA-encapsulated RBCs have a broader size distribution. The RNA-encapsulated erythrocytes maintain their normal morphology and impermeability after resealing in the specially formulated preservative medium.

Figure 5:
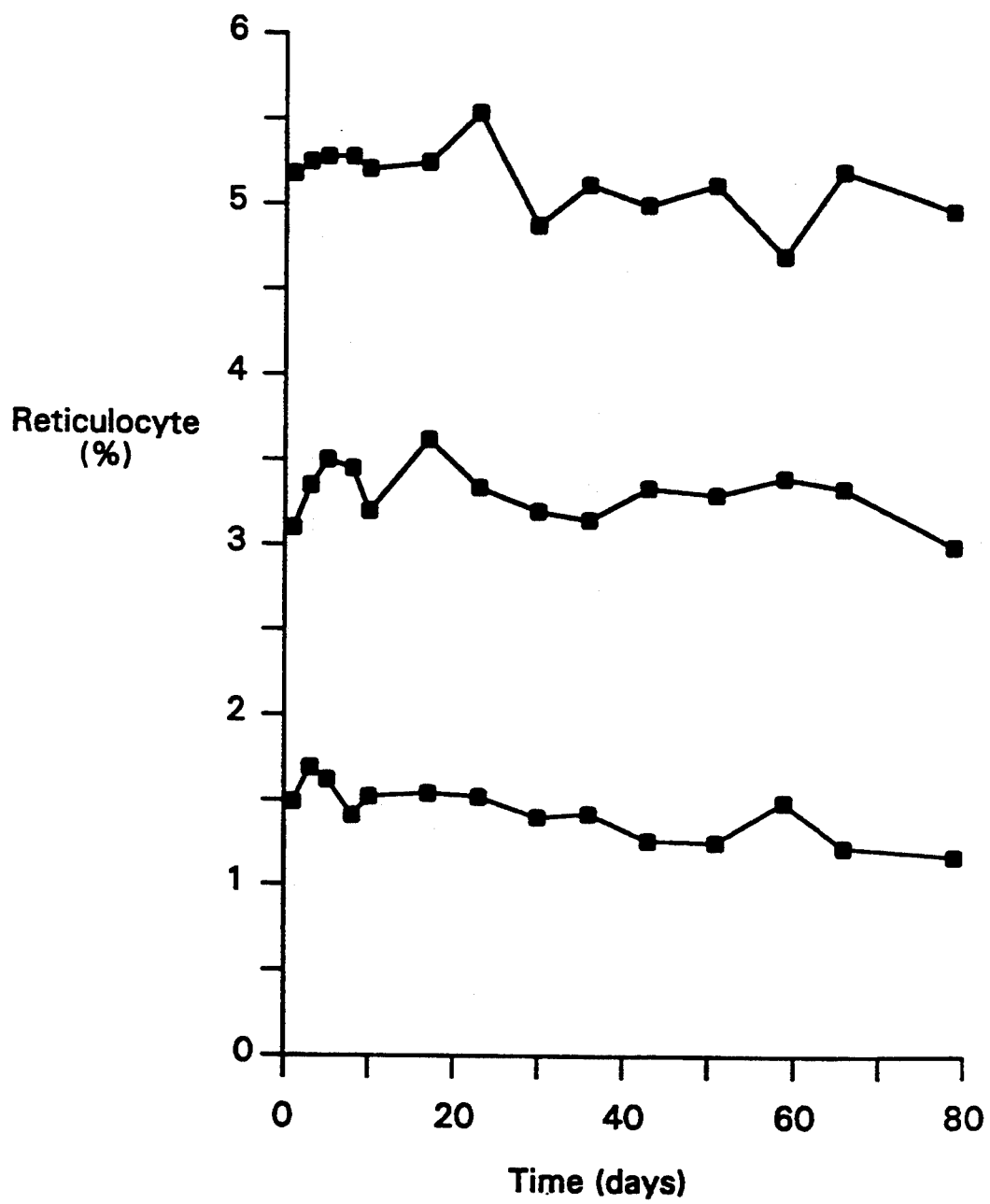
FIG. 5 is a graphic representation of the stability of a reticulocyte reference control of the present invention at three different reticulocyte levels at 6° C.

The reference control of the invention is long-lasting and provides stable human erythrocyte and reticulocyte populations for several months, i.e. 45 days. A typical stability plot of the reference control at three different reticulocyte levels at 6° C. is shown in FIG. 5. This plot shows stability at at least 80 days.

The synthetic reticulocytes which are used in the reference control of the invention exhibit a reticulocyte continuum and distribution that is similar to that of normal human reticulocytes. Furthermore, the synthetic reticulocytes of the invention can be stained with the various reticulocyte stains commonly used for both manual and flow cytometric reticulocyte counting. This is unlike the reticulocyte reference controls prepared by binding various fluorochromes to RBCs or polymer particles which exhibit a Gaussian reticulocyte distribution on the flow cytometers and which cannot be used for manual analysis.

Data obtained from the flow cytometric analysis using Sysmex R-1000 agrees very well with data obtained from manual counting using the reference control of the present invention. The reference control of the invention shows a nearly perfect regression linearity, and correlation coefficients of >0.99 are usually obtained in these comparison.

In the present invention, either RNA or a suitable polyanion can be used in the encapsulated RBCs of the reference control. Since cationic stains are used for manual and flow cytometric reticulocyte analysis, polyanions such as heparin can be encapsulated into erythrocytes, and polyanion-loaded RBCs can be used instead of RNA-loaded RBCs in the reference control of the invention with the same successful results. In counting procedures as carried out above with RNA, heparin-loaded RBCs showed similar reticulocyte characteristics as RNA-loaded RBCs. As those skilled in the art will appreciate, heparin may be obtained from bovine lung.

What is claimed is:

1. A method of determining the accuracy and reproducibility of the operation of a reticulocyte counting device, comprising the steps of:
   a) providing a reticulocyte reference control comprising a population of erythrocytes loaded with a nucleic acid, in an aqueous preserving medium, wherein the .reticulocyte reference control has a reference value of loaded erythrocytes representing the known number of erythrocytes loaded with a nucleic acid;
   b) staining the loaded erythrocytes;
   c) counting the number of loaded erythrocytes in the reference control with the counting device; and
   d) comparing the number of loaded erythrocytes obtained in step c) with the reference value of loaded erythrocytes in the reference control.

2. The method of claim 1, wherein the reticulocyte counting device is a manual device.

3. The method of claim 1, wherein the reticulocyte counting device is a flow cytometric device.

4. The method of claim 1, wherein the nucleic acid is ribonucleic acid.

5. The method of claim 4, wherein the ribonucleic acid is from Torula Yeast.

6. The method of claim 1, Wherein the nucleic acid is deoxyribonucleic acid.

7. The method of claim 1, wherein the loaded erythrocytes are human erythrocytes.

8. The method of claim 1, wherein the reticulocyte reference control further comprises a sufficient amount of non-loaded erythrocytes which serve to dilute the loaded erythrocytes in order to prepare controls with different levels of loaded erythrocytes.

9. The method of claim 1, wherein the population of erythrocytes are loaded with a nucleic acid using a reversible osmotic lysis procedure.

10. The method of claim 1, wherein the pH of the aqueous preserving medium is about 6.5–7.0.

11. The method of claim 1, wherein the osmolarity of the aqueous medium is about 300–350 mOsm/Kg.

12. A method of determining the accuracy and reproducibility of the operation of a reticulocyte counting device, comprising the steps of:
    a) providing a reticulocyte reference control comprising a population of erythrocytes loaded with a polyanion capable of binding to a cationic dye, in an aqueous preserving medium, wherein the reticulocyte reference control has a reference value of loaded erythrocytes representing the known number of erythrocytes loaded with a nucleic acid;
    b) staining the loaded erythrocytes;
    c) counting the number of loaded erythrocytes in the reference control with the counting device; and
    d) comparing the number of loaded erythrocytes obtained in step c) with the reference value of loaded erythrocytes in the reference control.

13. The method of claim 12, wherein the polyanion comprises heparin.

14. The method of claim 12, wherein the polyanion has a molecular weight of from about 10,000 to about 100,000 daltons.

15. The method of claim 12, wherein the cationic dye is selected from the group consisting of new methylene blue, acridine orange, auramine O, pyronine Y, thioflavin T and propidium iodine.

16. The method of claim 12, wherein the population of erythrocytes are loaded with a polyanion capable of binding to a cationic dye using a reversible osmotic lysis procedure.

17. The method of claim 12, wherein the reticulocyte reference control further comprises a sufficient amount of non-loaded erythrocytes which serve to dilute the loaded erythrocytes in order to prepare controls with different levels of loaded erythrocytes.

* * * * *